United States Patent [19]

Umetsu et al.

[11] Patent Number: 4,483,823

[45] Date of Patent: Nov. 20, 1984

[54] CHEMICAL ANALYZER EQUIPPED WITH REAGENT COLD-STORAGE CHAMBER

[75] Inventors: Hiroshi Umetsu, Katsuta; Hirotaka Sato, Hitachi; Katsuji Yamashita; Yoshimitsu Shibano, both of Katsuta, all of Japan

[73] Assignee: Hitachi, Ltd., Tokyo, Japan

[21] Appl. No.: 414,387

[22] Filed: Sep. 2, 1982

[30] Foreign Application Priority Data

Sep. 4, 1981 [JP] Japan .................. 56-138444

[51] Int. Cl.$^3$ .............................. G01N 35/00
[52] U.S. Cl. .................................. 422/63; 422/64; 422/67
[58] Field of Search ................... 422/63–67, 422/68, 99; 356/434; 62/526

[56] References Cited

U.S. PATENT DOCUMENTS

2,133,966 10/1938 Buchanan ..................... 62/526
4,325,910 4/1982 Jordan ........................ 356/434

Primary Examiner—Michael S. Marcus
Attorney, Agent, or Firm—Antonelli, Terry & Wands

[57] ABSTRACT

A chemical analyzer is disclosed in which a sample is supplied from a sample cup on a sample table to an array of reaction cups on a reaction table so that the reaction cups contain the same amount of sample, a reagent pipetting nozzle sucks an appropriate reagent solution from an array of reagent tanks and discharges the reagent solution into a corresponding reaction cup, the sample having reacted with the reagent solution is optically measured by a multi-wavelength photometer, a plurality of reagent tanks containing different reagent solutions are placed in a refrigerator with the openings of the reagent tanks being directed upward, the refrigerator is provided with a cover which has holes provided at positions corresponding to the openings of the reagent tanks, these holes are closed by a shutter except when the reagent pipetting nozzle is inserted into these holes, the array of reaction cups is immersed in constant-temperature-water contained in a reaction bath, the reaction bath is supplied with water which is kept at 37° C. in a liquid bath by means of an evaporator and a heater, and a refrigerant from a refrigerating machine passes through an evaporator provided in the refrigerator and the evaporator provided in the liquid bath to be returned to the refrigerating machine.

8 Claims, 11 Drawing Figures

CHEMICAL ANALYZER EQUIPPED WITH REAGENT COLD-STORAGE CHAMBER

The present invention relates to a chemical analyzer in which a cold-storage chamber carrying reagent tanks is cooled by a refrigerating machine, and more particularly to an improvement in an automatic analytical instrument disclosed in an application Ser. No. 268,353 filed by the present applicant in the United States on May 29, 1981 now abandoned.

In such an automatic analyzer of discrete type, a sample on a sample table is transferred by a sampling mechanism into a reaction cup on a reaction table. Then, an appropriate reagent solution is supplied into the reaction cup in accordance with an analyzing item. A colored condition of the sample which has reacted with the reagent solution, is measured optically by a photometer.

In this type of chemical analyzer, an array of reaction cups is mounted in a reaction bath, and immersed in a liquid kept at a constant temperature. Water kept at a predetermined temperature in the vicinity of ordinary temperature is supplied from a liquid bath which is provided with both a heater and a cooler, to the reaction bath to circulate through the liquid bath and reaction bath. It is required to control the temperature of the water with high accuracy, and therefore a temperature control mechanism for exclusive use in the liquid bath is employed. On the other hand, in order to prevent the degeneration of reagent solution, a number of reagent solutions are kept at a low temperature in a refrigerator. Another temperature control mechanism is employed to cool the air in the refrigerator. In a conventional analytical instrument, the two temperature control mechanisms with different load conditions are provided independently of each other.

An object of the present invention is to provide a chemical analyzer which has a function of keeping reagent solutions in cold storage and which moreover can be made small in size.

Another object of the present invention is to provide a chemical analyzer in which to-be-controlled objects with different load conditions can be simultaneously cooled by one refrigerating machine.

A further object of the present invention is to provide a chemical analyzer in which the temperature of a liquid supplied to a reaction bath can be controlled with high accuracy notwith-standing one refrigerating machine is used in common for a plurality of objects to be controlled.

According to the present invention, first cooling means is directly connected with second cooling means, a refrigerant having passed through the first and second cooling means is returned to a refrigerating machine, the first cooling means is provided in means for keeping a reagent in cold storage, the second cooling means is provided in means for keeping liquid at a constant temperature, and a liquid kept at a relatively-high, predetermined temperature by the means for keeping liquid at a constant temperature circulates the thermostatic means and a reaction bath to keep a reaction cup to a temperature suitable for the progress of reaction.

In a preferred embodiment of the present invention, an evaporator is used as the cooling means, and a refrigerator having a demountable cover is used as the means for keeping a reagent in cold storage. The cover is provided with a hole through which a reagent pipetting nozzle can be inserted into the reagent.

Figure 1:
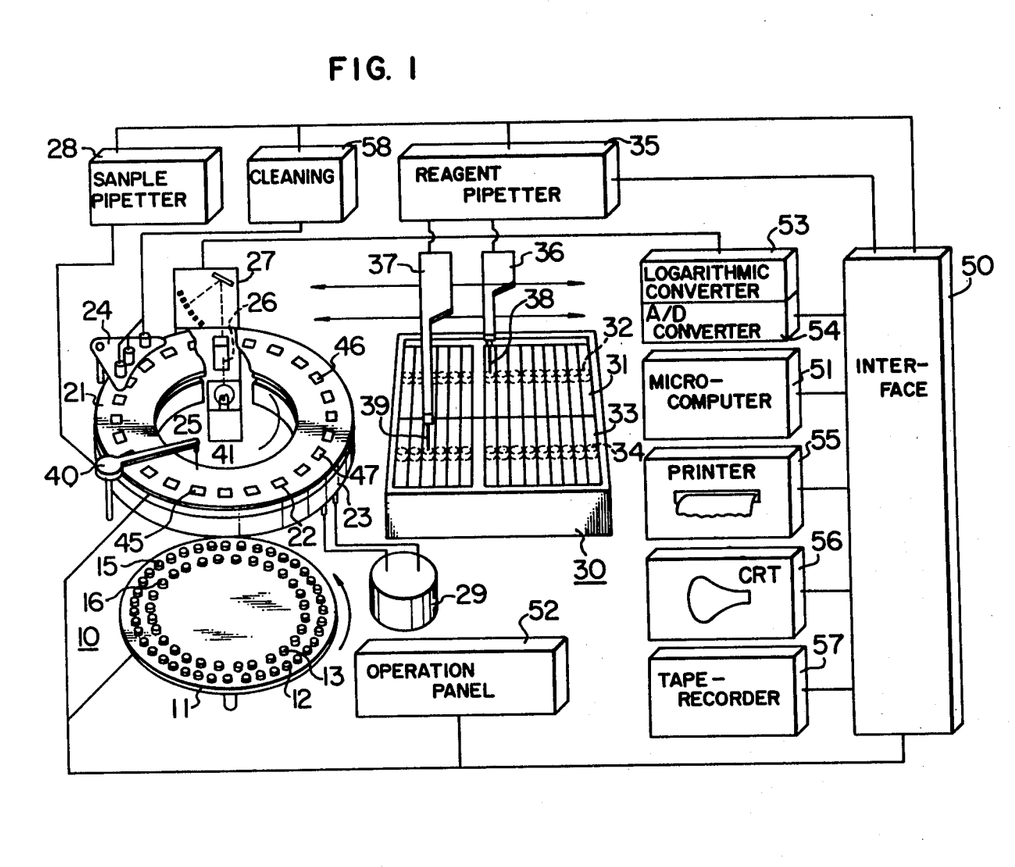
FIG. 1 is a schematic view showing the general construction of an embodiment of a chemical analyzer according to the present invention.
Figure 2:
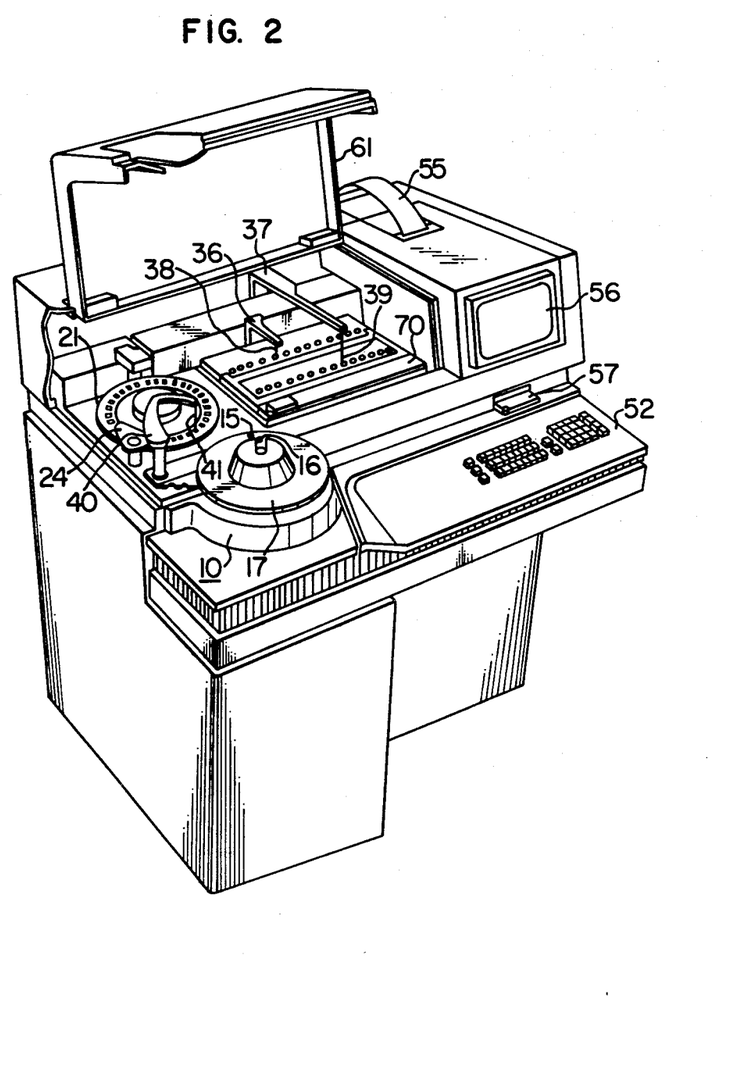
FIG. 2 is a view showing the exterior of the embodiment shown in FIG. 1.

Referring to FIGS. 1 and 2, in a sampler section 10, an array of sample cups 12 and another array of sample cups 13 are disposed on a sample table 11, and the sample cups are placed at sample sucking positions 15 and 16 at need. A sample pipetting nozzle 41 is hung from that arm of a sampling mechanism 40 which is rotatable in a horizontal plane. When the chemical analyzer is operated, a cover 17 is mounted on the sampler section 10. The cover 17 is provided with holes at the sample sucking positions 15 and 16.

A series of square-shaped reaction cups 22 are arranged on a reaction table 21, and an annular path 23 for the reaction cups 22 is disposed below the reaction table 21. Water kept at a constant temperature is introduced into the annular path 23, and a lower portion of each reaction cup is immersed in the constant-temperature water. Accordingly, the path 23 may be called a reaction bath. The constant-temperature water is supplied from a constant-temperature-water supply part 29 to the reaction bath 23. The temperature of water supplied to the reaction bath 23 is controlled by the constant-temperature-water supply part 29 so that the water is kept at a predetermined temperature in a range from 25° to 37° C., that is, in the vicinity of ordinary temperature. In some cases, the constant-temperature-water supply part 29 is called a liquid bath.

A reagent refrigerator 30 is disposed in proximity to the reaction table 21, and contains two lines of series-arranged reagent tanks 31 and 33. The tanks 31 and 33 are provided with openings 32 and 34, respectively. Each reagent tank is prepared in accordance with the kind of analyzing items. A cover 70 provided with two lines of holes for passing reagent pipetting nozzles 38 and 39 through the cover, is placed on the refrigerator 30. The reagent pipetting nozzles 38 and 39 are adapted to reciprocate independently of each other. In more detail, the reagent pipetting nozzle 38 is moved along the line of the openings 32 up to a reagent discharge position 46, while the reagent pipetting nozzle 39 is moved along the line of the openings 34 up to a reagent discharge position 47. The line of the reagent tanks 31 and that of the reagent tanks 33 are arranged in parallel, and the lines of the openings 32 and 34 are arranged in the same manner. The reagent tanks 31 and 33 have the form of a rectangular solid, and therefore a multiplicity of them can be arranged in closely adjacent relation to each other. The reagent pipetting nozzles 38 and 39 are stopped over respective openings of appropriate reagent tanks 31 and 33 in accordance with desired analyzing items, and moved down to take in and hold reagent solutions. Thereafter, the nozzles are moved upwardly, and then the reagent solutions held in the nozzles are discharged into reaction cups 22. The reagent pipetting nozzles 38 and 39 are cleaned at a cleaning section prior to suction of the reagent solutions.

Next, brief explanation will be made on the operation of the chemical analyzer.

The sample table 11 carrying a sample to be analyzed is mounted on the sampler 10, and a start button on an operation panel 52 shown in FIGS. 1 and 2 is depressed to start the operation of the chemical analyzer. The sample pipetting nozzle 41 of the sampling mechanism 40 sucks and holds the sample at the sample sucking position 15 or 16 by the action of a sample pipetter 28, and discharges the held sample at a sample discharge position 45. The array of reaction cups 22 is transferred to cross a light beam 26, and the reaction table 21 makes one revolution plus one step so that the reaction cup next to one which has received the sample, is placed at the sample discharge position 45. This sampling operation is continuously repeated. When the reaction table 21 is stationary, nozzles of a cleaner 24 are inserted into reaction cups placed at predetermined positions to perform a cleaning operation.

When the reaction table 21 is stationary, a reagent solution is supplied into a reaction cup placed at a reagent discharge position 46 or 47. Thus, a color reaction is started in the reaction cup. For an analyzing item requiring only one reagent solution, the reagent solution is supplied into the reaction cup placed at the reagent discharge position 47 only with the aid of the movement of a reagent pipetting portion 37. Samples for various analyzing items can be disposed on the reaction table. In one method, one sample is distributed among reaction cups, the number of which is equal to the number of analyzing items, for example, among 16 reaction cups. Similarly, the next sample is distributed among 16 reaction cups. Then, reagent solutions corresponding to the analyzing items are supplied into desired reaction cups through the aid of the movement of the reagent pipetting portions 36 and 37.

The reagent pipetting portions 36 and 37 are hung from rails, and are capable of moving along the rails. The reagent pipetting portions 36 and 37 can also move vertically together with the rails. The reagent pipetting nozzles 38 and 39 can be stopped at the openings 32 and 34 of the reagent tanks, if required. The operation of the drive mechanism of each of the reagent pipetting portions 36 and 37 is controlled by a microcomputer 51. The reagent solutions corresponding to analyzing items for the sample which has reached the discharge positions 46 and 47, are selected by the reagent pipetting portions 36 and 37, and the pipetting nozzles 38 and 39 temporarily stop over the corresponding reagent tanks 31 and 33. Simultaneously with the above operation, shutters 702A and 702B provided on the cover 70 of the reagent refrigerator 30 are put in an open state so that holes 701A and 701B appear. (Refer to FIGS. 7 and 9.) Subsequently, the pipetting portions 36 and 37 move down in order for a reagent pipetter 35 to cause each of the pipetting nozzles 38 and 39 to suck and hold a predetermined amount of reagent solution. Then, the pipetting portions 36 and 37 move upward. Immediately after the upward movement of the pipetting portions 36 and 37 has been completed, the shutters 702A and 702B are put in a closed state, and the nozzles 38 and 39 are horizontally moved above the shutters to the reagent discharge positions 46 and 47, to discharge the reagent solutions held by the nozzles into the corresponding reaction cups.

Since the reaction table 21 is turned each time a sampling operation is performed, the sample in the reaction cup crosses a light beam 26 from a light source 25 at each turning motion, and thereby a colored condition of the sample can be observed. In other words, the optical characteristics of the same sample can be observed a plurality of times before the reaction cups reach the position of the cleaning machine 24.

A wavelength component required for an analyzing item is selected by a wavelength selection circuit (not shown) from light received by the photoelectric detector of a multi-wavelength photometer 27, and an electric signal of a magnitude corresponding to the intensity of a transmitted light is applied to a logarithmic converter 53. Then, an analog signal from the converter 53 is converted by an A/D converter 54 into a digital signal. The digital signal is led through an interface 50 to the microcomputer 51, in which required operations are performed and the result thereof is stored in a memory. When a plurality of photometric operations for a specified analyzing item are all completed, the plurality of photometric data are compared with each other and required calculations are made to print out a concentration value with respect to the analyzing item by a printer 55.

An analytical condition at each measuring item and measured data are stored in a cassette tape which can be set in a cassette tape recorder 57. A cleaning syringe mechanism 58 is connected to pipes of the cleaning machine 24, and includes vacuum and discharge syringes for sucking and injecting the cleaning water.

According to the present embodiment, analysis can be made by the colorimetric method and the reaction rate method. Incidentally, a nozzle cleaning part (not shown) is disposed in the vicinity of the sample table 11, and another nozzle cleaning part (not shown) is disposed in the vicinity of the reagent refrigerator 30. In the present embodiment, conditions of analysis are stored in a cassette tape. Accordingly, the analyzing item can be changed in such a manner that a desired condition of analysis is read out of the cassette tape by the tape recorder 57 and a different reagent tank is selected. Since the embodiment adopts the reagent pipetting method, when the reagent tank is exchanged, it is not required to clean a flow path system. Further, since reagent solutions are kept at a low temperature in the refrigerator, the composition of each reagent solution scarcely varies, and therefore the reagent solutions can be used for a long time. Further, since the cover 70 is mounted and detached at an upper portion of the refrigerator, a small amount of cold air is lost when the cover is detached. Thus, when the reagent solutions in the refrigerator are exchanged, the cooling ability of the refrigerator is lowered only a little. The shutters 702A and 702B provided on the cover 70 prevent the reagent tanks from being contaminated by accidental dropping of reagent solution from the nozzles 38 and 39.

The analyzing items and conditions of analysis by items can be inputted by means of a cathode ray tube, item keys, profile keys and ten keys.

Figure 3:
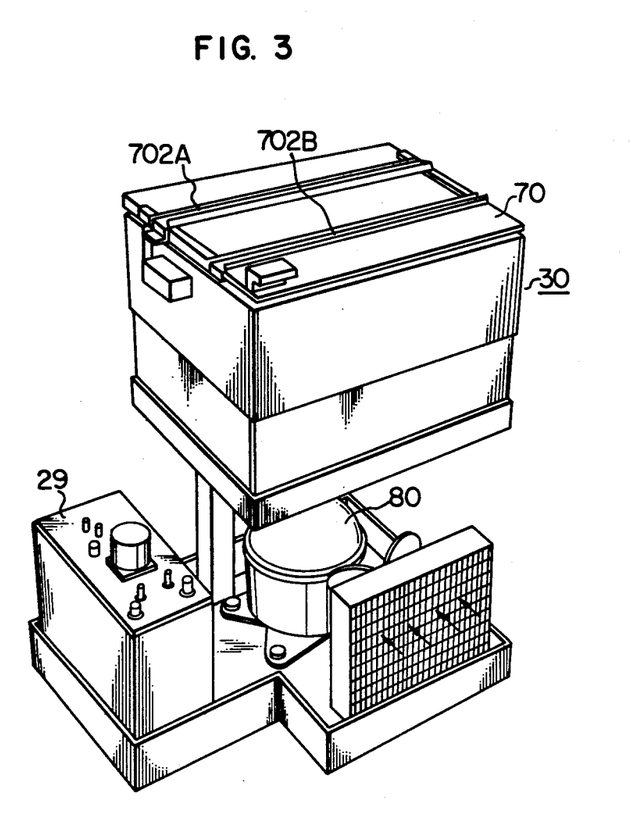
FIG. 3 is a schematic view showing the exterior of a reagent refrigerator and adjacent parts.

Next, the reagent refrigerator will be explained below in detail, with reference to FIGS. 3 to 9. The refrigerator 30 shown in FIG. 3 is the combination of a box shown in FIG. 4 and the cover 70 shown in FIG. 7, and is refrigerated by a refrigerating machine 80. The constant-temperature-water supply part 29 supplied the reaction bath 23 with constant-temperature water. The cover 70 is provided with shutters 702A and 702B over which the pipetting nozzles 38 and 39 are moved along the shutters 702A and 702B.

Figure 4:
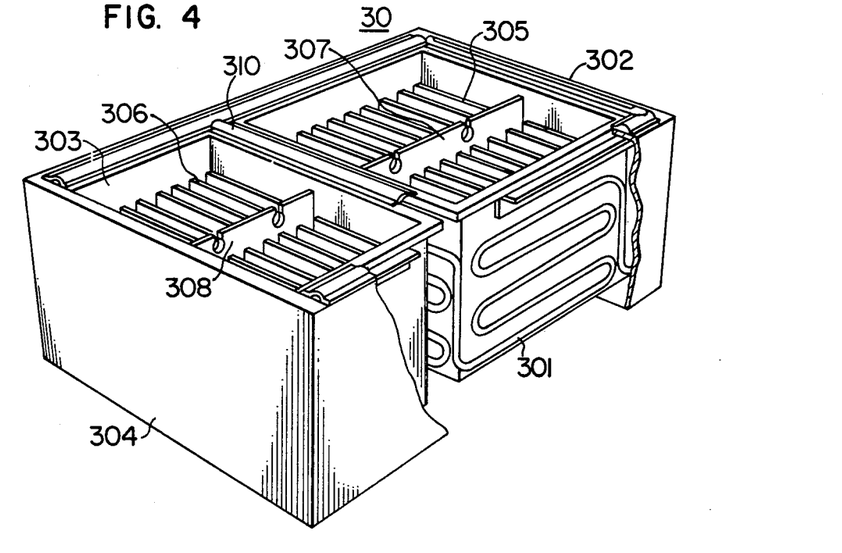
FIG. 4 is a partially cutaway view of the reagent refrigerator.
Figure 5:
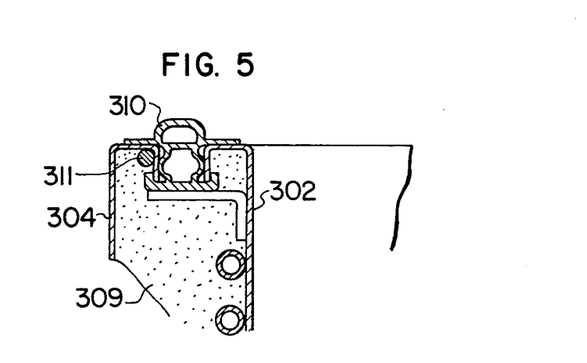
FIG. 5 is a sectional view of the wall of the refrigerator.

Referring to FIGS. 4 and 5, an evaporator 301, through which a refrigerant gas flows, is attached to all side walls of the cold storage box 302 by welding or the like. A container 303 is kept at room temperature. Both of the cold storage box 302 and container 303 are enclosed by an outer wall 304 of the refrigerator 30. A space between the outer wall 304 of the refrigerator 30 and the side walls and lower surface of the cold storage box 302 is filled with a heat insulating material 309. A heat insulating packing 310 is fitted between the cold storage box 302 and container 303 to prevent the container 303 from being refrigerated. In order to prevent the outer wall 304 from getting wet with dew due to heat transfer from the wall 304 to the inside of the cold storage box 302 when the atmosphere is high in humidity or temperature, a heater 311 is provided all over the inner side of the outer wall 304. Partition boards 305 and 306 are demountably provided within the cold storage box 302 and container 303 so that the reagent tanks 31 and 33 can be fixed at predetermined positions. The partition boards 305 and 306 can be taken out of the cold storage box 302 and container 303 by lifting intermediate plates 307 and 308.

Figure 6:
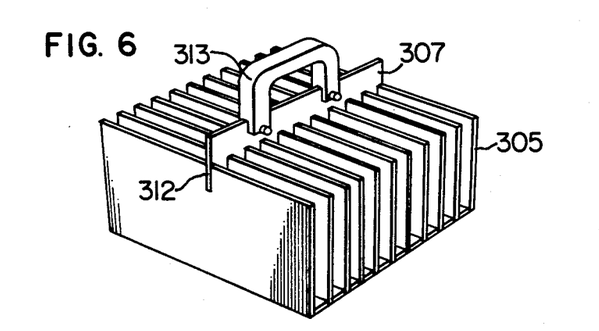
FIG. 6 is a view showing the structure of partition boards provided in the refrigerator.

The partition board 305 and intermediate plate 307 placed in the cold storage box 302 will be explained with reference to FIG. 6. The intermediate plate 307 is provided at an upper portion thereof with two grooves, each of which has a narrow opening as shown in FIG. 4. On the other hand, each of a plurality of partition boards 305 is provided at an upper portion thereof with a deep groove 312, into which the intermediate plate 307 is pressed. After the intermediate plate 307 has been pressed into respective grooves 312 of the partition boards 305, the intermediate plate 307 is fixed to the partition boards 305 by welding or the like. A grip 313 is used for lifting the intermediate plate 307.

Figures 7, 8:
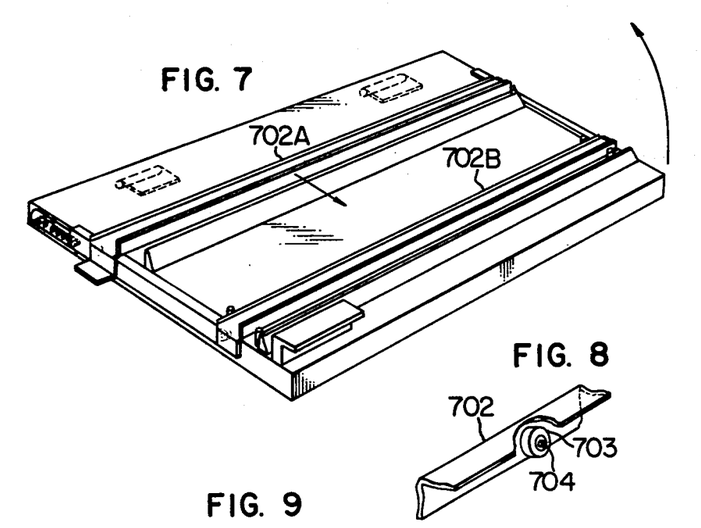
FIGS. 7 to 9 are views for explaining the structure of a cover mounted on the refrigerator.
Figure 9:
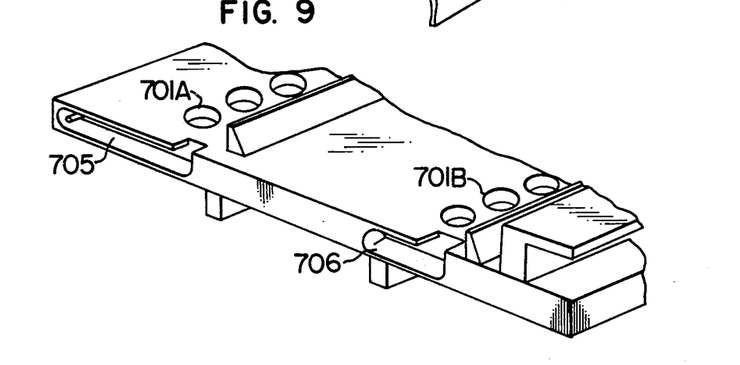

The cover 70 is provided with holes 701A and 701B which agree, in position, with the openings 32 and 34 of the reagent tanks 31 and 33. On the cover 70 are mounted the shutters 702A and 702B. Each shutter is ordinarily put in a closed state, and put in an open state only when the reagent pipatting nozzles 38 and 39 such reagent solutions, in a manner as moved in a lateral direction, and is, in a direction indicated by an arrow. At both ends of each of the shutters 702A and 702B, a pin 704 is attached to the shutter and a ball bearing 703 is mounted rotatably around the pin 704 as shown in FIG. 8. The ball bearing 703 is put into and turned in a groove 705 or 706, which is bored in opposite end surfaces of the cover 70 at four positions as shown in FIG. 9.

Figure 10:
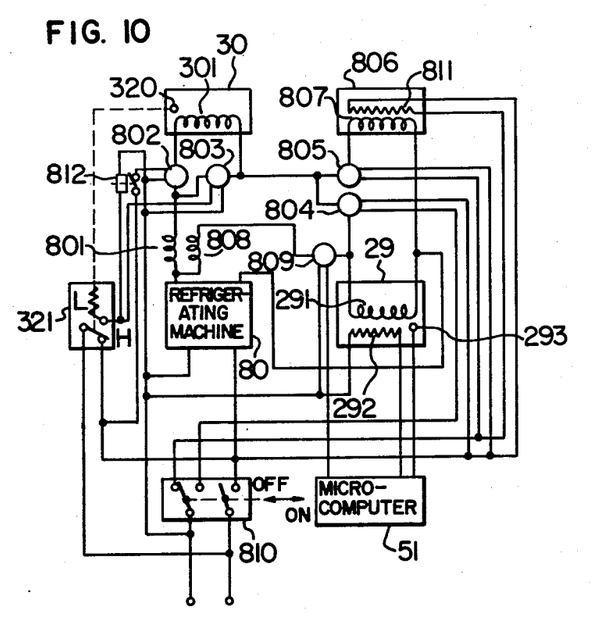
FIG. 10 is a view for explaining a temperature control system used in the embodiment shown in FIG. 1.

FIG. 10 shows the cooling pipe arrangement (thick lines) and electric control circuit of the present embodiment. The refrigerating machine 80 is made up of a compressor, a liquid receiver, a condenser and others, though the detailed structure of the machine 80 is not shown in FIG. 10. A refrigerant gas sent out from the refrigerating machine 80 passes through one capillary tube 801, and then divided into two parts, one of which is led to a solenoid valve 802 and the other is led to a solenoid valve 803. The solenoid valve 802 is connected to the evaporator 301 attached to the reagent refrigerator 30. Further, the solenoid valve 803 is connected to the exit of the evaporator 301. The electric control circuit is constructed so that one of the solenoid valves 802 and 803 is made open when the other solenoid valve is closed.

The refrigerant gas having passed through the reagent refrigerator 30 is divided into two parts, one of which is led to a solenoid valve 804 and the other is led to a solenoid valve 805. The solenoid valve 804 is connected to an evaporator 291 in the liquid bath 29 for obtaining constant-temperature water. The solenoid valve 805 is connected to an evaporator 807 in a cooler 806, and respective exits of the evaporators 291 and 807 are connected to each other to be connected to the refrigerating machine 80. The control circuit is constructed so that one of the solenoid valves 804 and 805 is made open when the other solenoid valve is closed.

Another flow path starting from the refrigerating machine 80 passes through a capillary tube 808, and reaches a solenoid valve 809. The exit of the solenoid valve 809 and that of the solenoid valve 804 are united in one exit. The solenoid valves 802 and 803 are electrically connected to a contact 321 which is operated by a thermostat 320 attached to the cold storage box 302 in the reagent refrigerator 30. When the temperature in the cold storage box 302 becomes lower than a set value, the contact 321 is connected to an L-side, thereby closing the solenoid valve 802 and opening the solenoid valve 803. The solenoid valves 804 and 805 are controlled by a main switch 810 of the analyzer. When the switch 810 is set to the ON-side, the solenoid valve 804 is made open to cool water in the constant-temperature-water supply part 29. The part 29 is provided therein with a heater 292 and a thermistor 293 for detecting water temperature. The heater 292 is controlled by the microcomputer 51 so that the water is kept at a constant temperature. The cooler 806 is provided with a heater 811 for raising the temperature in the cooler 806. A relay 812 is connected to the L-side of the contact 321 to make and break the drive circuit of the solenoid valve 802.

In the case where the reagent refrigerator 30 is continuously operated day and night and the constant-temperature-water supply part 29 is operated only during the day when samples are analyzed and measured, the changeover of the operation is made by the main switch 810. In more detail, when the main switch 810 is set to the OFF-side, the refrigerating machine 80, solenoid valves 802 and 805, and heater 811 are operated in the state that the contact 321 is connected to the H-side, and thus the refrigerant gas flows to cool the refrigerator 30. At this time, the refrigerant gas passes through the capillary tube 801, solenoid valve 802, evaporator 301, solenoid valve 805 and evaporator 807, and then returns to the refrigerating machine 80. When the refrigerator 30 is cooled to a predetermined temperature, the thermostat 302 is operated, and therefore the contact 321 is connected to the L-side. Thus, the solenoid valve 803 is made open, and further the relay 812 is operated to close the solenoid valve 802. That is, the gas flow path to the refrigerator 30 is completely closed. At this time, the refrigerant gas is not supplied due to the operation stoppage of the refrigerating machine 80, but flows till a pressure difference in the compressor becomes zero, that is, the reagent refrigerator 30 is cooled. Therefore, it is required to close the solenoid valve 802.

The refrigerating machine in the present embodiment not only keeps the reagent solutions in cold storage, but also acts as a cooling source for maintaining the water in the constant-temperature-water supply part 29 at a constant temperature, for example, 25°, 30°, or 37° C. with a precision of ±0.05° C. In other words, the refrigerator 30 is of the air cooling type, and the constant-temperature-water supply part 29 is of the water cooling type. A cooling apparatus in which to-be-cooled objects having different load conditions are connected in series and are cooled by one refrigerating machine, has been hitherto unknown. When the main switch 810 is set to the OFF-side and the contact 321 of the thermostat 320 is connected to the H-side, the cooler 806 which gives the refrigerating machine 80 a load substantially equal to the constant-temperature-water supply part 29, is connected to the refrigarator 30, and therefore the day and night operation and the day-operation are made under the same load condition.

As mentioned previously, it is required to control the temperature of water in the constant-temperature-water supply part 29 with a precision of ±0.05° C. Therefore, the evaporator 291, heater 292 and thermistor 293 are immersed in the water within the constant-temperature-water supply part 29. Usually, the refrigerant gas flows through the evaporator 291 at a constant flow rate. However, when the solenoid valve 803 is closed and the solenoid valve 802 is opened by the operation of the thermostat 320 attached to the refrigerator, gas having cooling ability temporarily does not flow through the evaporator 291 in the liquid bath 29 due to a difference in length of gas flow path. As a result, even when the operation of the heater 292 is stopped, the temperature of water is raised by about 0.20° C. due to the heat left in the heater 292. In order to prevent such a temperature drift, a bypass is provided which is made up of the capillary tube 808 and solenoid valve 809. That is, in view of the above-mentioned temperature drift, the bypass has been devised. The solenoid valve 809 which is controlled by the microcomputer 51 independently of the operation of the solenoid valves 802 and 803, is closed only when the refrigerator 30 is first cooled and usually made open. Accordingly, the refrigerant gas alway flows through the evaporator 291 in the liquid bath 29, and therefore the temperature drift is completely prevented.

Figure 11:
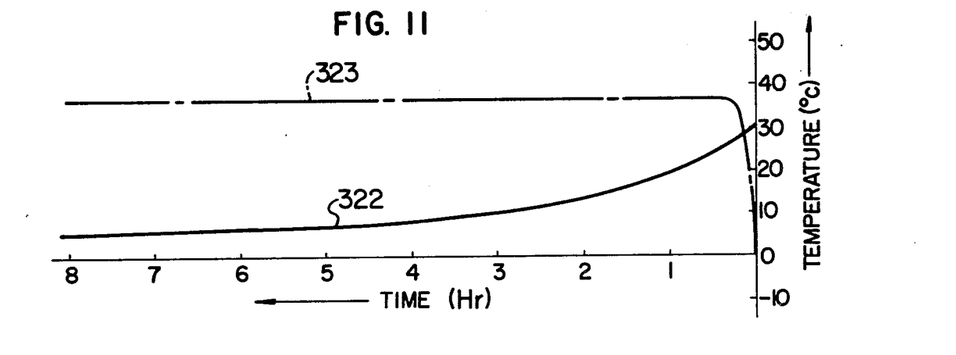
FIG. 11 is a graph showing respective temperature characteristics of the reagent refrigerator and a reaction bath.

Referring to FIG. 11, when the analyzer is operated, the temperature in the reagent tanks 31 and 33 varies in accordance with a smooth cooling curve 322, and the temperature of water in the reaction bath 23 is controlled as indicated by a curve 323, that is, reaches a constant value in a short time.

We claim:

1. A chemical analyzer comprising:
a reaction bath containing a liquid for immersing therein an array of reaction cups, said reaction cups containing a sample to be analyzed and a reageant;
means for analyzing said sample, with said reagent, operatively associated with said reaction cups;
refrigerant conduit means including first and second series-connected evaporators for supplying a refrigerant from a refrigerating machine to said second evaporator through said first evaporator and then returning said refrigerant to said refrigerating machine;
reagent cold-storage means having a chamber capable of retaining a plurality of reagent tanks, said first evaporator being disposed in said reagent cold-storage means, air in said chamber being cooled by said first evaporator so as to be kept at a predetermined temperature;
liquid bath means for maintaining said liquid supplied to said reaction bath at a predetermined temperature in the vicinity of ordinary temperature, said second evaporator being disposed in said liquid bath means and;
bypass conduit means providing one flow path in parallel with said first evaporator and another flow path in parallel with said second evaporator whereby said refrigerant is allowed to by-pass at least one of said first and said second evaporators when the temperature therein falls below the predetermined temperature.

2. A chemical analyzer according to claim 1, wherein said flow path provided in parallel with said second evaporator is provided with a cooler.

3. A chemical analyzer according to claim 1, wherein said flow path provided in parallel with said first evaporator is provided with a valve, and said flow path provided in parallel with said second evaporator is provided with a valve.

4. A chemical analyzer according to claim 1, further including conduit means providing a flow path for continuously supplying said refrigerant from said refrigerating machine to said second evaporator when said liquid bath means is operated.

5. A chemical analyzer comprising:
reagent cold-storage means having a chamber capable of retaining a plurality of reagent tanks;
analyzing means operatively associated with said reagent tanks for analyzing a sample with a reagent from at least one of said reagent tanks;
a first evaporator for cooling said reagent cold-storage means;
liquid bath means for maintaining a liquid at a predetermined temperature;
a second evaporator for controlling the temperature of said liquid bath means;
first conduit means providing a circulating flow path through which a refrigerant exiting from a refrigerating machine returns to said refrigerating machine through said second evaporator after passing through said first evaporator;
second conduit means providing a first bypassing flow path for allowing said refrigerant to pass therethrough when said refrigerant is prevented from flowing into said first evaporator, said first bypassing flow path being arranged in parallel with said first evaporator; and
third conduit means providing a second by passing flow path for allowing said refrigerant to pass therethrough when said refrigerant is prevented from flowing into said second evaporator, said second bypassing flow path being arranged in parallel with said second evaporator, said second bypassing flow path being provided with a third evaporator.

6. A chemical analyzer according to claim 5, in which said reagent cold-storage means has no heater and the temperature of said reageant cold-storage means is controlled by actuating means for opening/closing a flow path in said circulating flow path for conducting the refrigerant to said first evaporator, and in which said liquid bath means has a heater so that the temperature of said liquid bath means is controlled by action of said second evaporator and said heater.

7. A chemical analyzer comprising:

reagent cold-storage means for cooling a plurality of reagent containers;

analyzing means operatively associated with said reagent containers for analyzing a sample with a reagent taken from at least one of said reagent containers;

a first evaporator for cooling said reagent cold-storage means;

liquid bath means for maintaining a liquid at a predetermined temperature;

a second evaporator for cooling the temperature of said liquid bath means;

a first conduit means providing a flow path through which a refrigerant exiting from a refrigerating machine is passed via said first and said second evaporators;

second conduit means providing a bypassing flow path disposed in parallel with said second evaporator, said bypassing flow path including a third evaporator operatively associated with a cooler providing a predetermined load; and flow path opening/closing means for preventing the refrigerant from flowing into said second evaporator via said first conduit means while conducting the refrigerant to said third evaporator via said second conduit means during stoppage of the analyzing operation of said chemical analyzer, and for preventing the refrigerant from flowing into said third evaporator while conducting the refrigerant to said second evaporator during performance of the analyzing operation of said chemical analyzer.

8. A chemical analyzer according to claim 7, in which said refrigerating machine operates so that the refrigerant can be supplied to said first evaporator via said first conduit means even during stoppage of the analyzing operation of said chemical analyzer.

* * * * *